United States Patent [19]

Takagi et al.

[11] Patent Number: 4,793,700

[45] Date of Patent: Dec. 27, 1988

[54] GAZE-FIXING DEVICE FOR SURGICAL MICROSCOPE

[75] Inventors: Kazutoshi Takagi; Nobuaki Kitajima, both of Tokyo, Japan

[73] Assignee: Tokyo Kogaku Kikai Kabushiki Kaisha, Tokyo, Japan

[21] Appl. No.: 28,895

[22] Filed: Mar. 23, 1987

[30] Foreign Application Priority Data

Mar. 26, 1986 [JP] Japan .................................. 61-68099

[51] Int. Cl.⁴ .......................... A61B 3/10; G02B 21/06
[52] U.S. Cl. ..................................... 350/507; 350/520; 351/211
[58] Field of Search ....................... 350/526, 507, 520; 351/207–208, 211–213, 221

[56] References Cited

U.S. PATENT DOCUMENTS

| | | | |
|---|---|---|---|
| 3,416,855 | 12/1968 | McClernon | 351/212 |
| 4,208,107 | 6/1980 | Oharek | 351/221 |
| 4,283,124 | 8/1981 | Matsumura | 351/211 |
| 4,478,499 | 10/1984 | Herenz | 351/211 |
| 4,614,411 | 9/1986 | Horenz | 351/211 |

OTHER PUBLICATIONS

Dale, W., "Fixation Device as an Aid to Fundus Examination" J. R. of the American Optometric Ass. 7-1959, pp. 869-870.
Knoll et al., "The Ophthalmetron, Principles and Operation" American Jr. of Optometry & Archives of American Academy of Optometry 2-1972; pp. 122-128.

Primary Examiner—John K. Corbin
Assistant Examiner—Martin Lerner
Attorney, Agent, or Firm—Brumbaugh, Graves, Donohue & Raymond

[57] ABSTRACT

A gaze-fixing device for a surgical microscope which is capable of providing a marking without an error at the time of a radial keratotomy operation. The device comprises a gaze-fixing target which can be disposed on the observation optical axis of a microscope, and light quantity-reducing means for reducing the quantity of illumination light applied from an illumination light source for illuminating an eye to be operated on.

5 Claims, 4 Drawing Sheets

GAZE-FIXING DEVICE FOR SURGICAL MICROSCOPE

BACKGROUND OF THE INVENTION

The present invention relates to a gaze-fixing device installed or incorporated in a surgical microscope and adapted to fix the gaze of a patient to be operated on, and, more particularly, to a gaze-fixing device useful for radial keratotomy.

In recent years, surgical operations of radial keratotomy (hereafter referred to as the "RK operation") have come to be undertaken in which radial cuts are provided in a cornea for treating abnormalities of refraction of an eye, such as myopia and astigmatism. It is necessary to provide a marking at the central position of the cornea so as to effect this RK operation.

For this purpose, a conventional surgical microscope has a gaze-fixing device whereby, as shown in FIG. 7, the patient being operated on is made to gaze at a light source LS of a concentric illuminator CI, along a visual axis VA a reflected image F' of the filament F of the light source LS formed by the cornea C of the eye E to be operated on is observed by a microscope MS, and a cornea-passing point P of a principal ray PR from this reflected image F' is marked as the center of the cornea.

With this conventional device, as can be seen from FIG. 7, since the eye to be operated on gazes at the filament F of the light source LS, the visual axis VA thereof differs from the observation optical axis OA for observing the reflected image F' of the microscope MS, and also differs from the principal ray PR directed from the reflected image F' to an observation optical system. Consequently, if a conventional device is used, a marking cannot be provided at the real center Q of the cornea where the visual axis VA passes through the cornea C, so that there has been a drawback that the marking is provided at the cornea-passing point P of the principal ray PR, which is different from the same.

In addition, the conventional device has had another drawback in that stimulus on the fovea centralis macula retinae of the eye to be operated on is too strong since the patient fixes his gaze on the filament of a high-illuminace light source which is used during the operation. Furthermore, although the conventional surgical microscope is provided with a light quantity-adjusting means, the adjusting means is installed at the power source portion of the microscope. Hence, the operator, who has undergone sterilization treatment, cannot operate it directly, and an assistant has been necessary. This problem of adjusting the quantity of illumination light arises not only in connection with the RK operation alone, but also in connection with other ophthalmologic operations.

SUMMARY OF THE INVENTION

The present invention has been devised to overcome the aforementioned drawbacks of the prior art, and a principal object of the invention is to provide a gaze-fixing device for a surgical microscope which is capable of providing a marking without an error at the time of an RK operation.

Another object of the invention is to provide a gaze-fixing device for a surgical microscope which does not apply an excessive stimulus of light to the fovea centralis macula retinae when the eye to be operated on is at a fixed gaze.

According to the present invention, the above and other objects can be accomplished by a gaze-fixing device for a surgical microscope, comprising a gaze-fixing target which can be disposed on the observation optical axis of a microscope and a light quantity-reducing means for reducing the quantity of illumination light applied from an illumination light source for illuminating the eye to be operated on.

In a preferrable aspect of the present invention, said gaze-fixing target is constituted by a light-emitting end of light-conducting means for receiving part of said illumination light and disposed on said optical axis.

In another aspect of the present invention, said light-conducting means is an optical fiber.

In another aspect of the present invention, said gaze-fixing target and said light quantity-reducing means are arranged such that they can be simultaneously inserted in and removed from said optical axis and an illumination optical path, respectively, by means of the movement of said base plate.

The above and other objects and features of the present invention will become apparent from the following descriptions of the preferred embodiments with reference to the accompanying drawings.

DESCRIPTIONS OF THE DRAWINGS

DESCRIPTION OF THE PREFERRED EMBODIMENTS

In accordance with the above-described arrangement, since the gaze-fixing target is located on the observation optical axis of the microscope, the visual axis of the eye to be operated on which fixedly gazes at the same coincides with the observation optical axis of the microscope, and the principal ray from the reflected image of the gaze-fixing target to the microscope, which is formed on the visual axis, also coincides with the observation optical axis.

In addition, since a light quantity-reducing means for the gaze-fixing target is provided, the quantity of light for the gaze-fixing target for the eye to be operated on is reduced to an appropriate level.

ARRANGEMENT OF ESSENTIAL PARTS OF THE MAIN BODY OF MICROSCOPE

Figure 1:
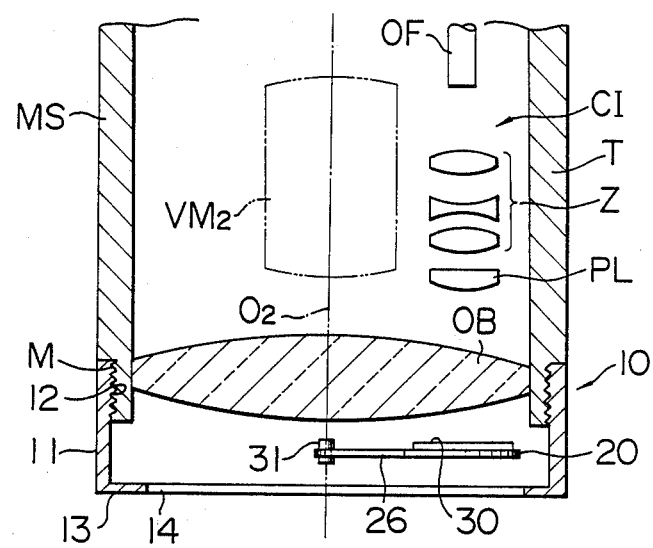
FIG. 1 is a cross-sectional view of essential portions of a first embodiment of a gaze-fixing device in accordance with the present invention together with the main body of a microscope.

FIG. 1 illustrates essential parts of the main body of a surgical microscope in which a gaze-fixing device in accordance with the present invention is installed. In the main body MS of the microscope, zoom variable magnification and image formation systems VM1, VM2

(only VM2 is shown in FIG. 1) of a binocular observation optical system of a single object lens OB, and a concentric illumination optical system CI are incorporated in a lens-barrel T.

The concentric illumination optical system CI is constituted by an optical fiber OF which guides light from a high-illuminance light source (not shown), e.g., a halogen lamp having the maximum rated illuminance of 120,000 lux, a zoom optical system Z for converting an illumination field, and a projection lens PL.

The illumination light from the optical fiber OF is projected onto an eye to be operated on (not shown) via the zoom optical system Z, the projection lens PL, and the single object lens OB. The image of the eye to be operated on is viewed three-dimensionally by the operator through an erect optical system and an occular (neither is shown) via the single object lens OB and the zoom variable magnification and image formation systems VM1, VM2. A male screw portion M is formed at the tip of the lens-barrel T.

First Embodiment

Figure 2:
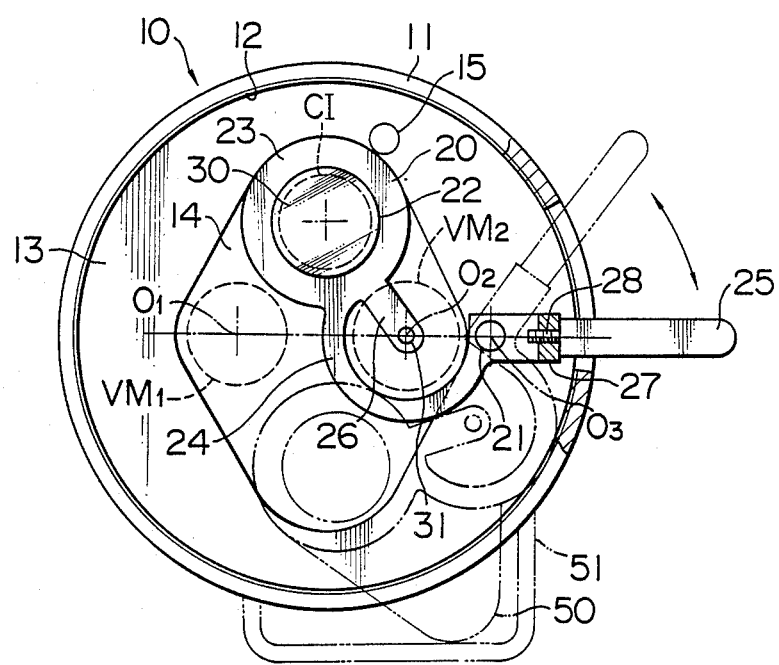
FIG. 2 is a top plan view of the first embodiment.

FIGS. 1 and 2 show a first embodiment of a gaze-fixing device in accordance with the present invention. A female screw portion 12 is formed in a casing 11 of a gaze-fixing device 10, and the gaze-fixing device 10 can be installed by engaging the female screw portion 12 with the male screw portion M of the main body MS of the microscope. An opening 14 which does not block the entrance fields of at least the illumination optical system CI and the zoom variable magnification and image formation systems VM1, VM2 is formed on a bottom surface 13 of the casing 11. In addition, a shaft 21 is embedded in the bottom surface 13 to provide a rotary axis $O_3$ which is located within a plane including respective optical axes $O_1$, $O_2$ of the zoom variable magnification and image formation systems VM1, VM2 and is parallel with the optical axes $O_1$, $O_2$.

A rotary base plate 20 is rotatably supported by the shaft 21 with the rotational axis $O_3$ as its center so as to be rotatable. The rotary base plate 20 is constituted by a disk portion 23, an arm 24, a lever 25, and a gaze-fixing target arm 26.

An opening 22 for allowing light from the illumination optical system CI to be transmitted therethrough is formed in the rotary base plate 20, and an ND filter which has a transmittance of approximately 1% and serves as a light quantity-reducing means is adhered to the upper portion thereof. The disk portion 20 has a gaze-fixing target arm 26 extending radially toward the optical axis $O_2$ of one zoom variable magnification and image formation system VM2. At the tip of this gaze-fixing target arm 26 is installed a gaze-fixing target 31 constituted by a light-emitting diode which emits light of a red color by making the optical axis $O_2$ of the zoom variable magnification and image formation system VM2 to coincide with a point of luminance.

The arm 24 is curved so that when it is installed at a position (hereafter referred to as the "set position") for making the gaze-fixing target 31 coincide with the optical axis $O_2$, the arm 24 will not block the entrance field of the zoom variable magnification and image formation system VM2. The lever 25 is so arranged as to screw the male screw portion 28 onto the female screw portion 27 of the arm 24, and is arranged such that this screw engagement can be released so that the lever 25 alone can be subjected to sterilization treatment.

The peripheral surface of the disk portion 23 abuts against the vicinity of the opening 14 of the bottom surface 13, and a restriction pin 15 is embedded therein for restricting the coincidence of the rotary disk plate 20 with the set position, i.e., the coincidence of the gaze-fixing target 31 with the optical axis $O_2$.

Description of the operation of the present embodiment will be described hereafter. The lever 25 is rotated clockwise until the peripheral surface of the disk portion 23 is brought into contact with the restriction pin 15, and the gaze-fixing target 31 is made to coincide with the optical axis $O_2$. At that time, the ND filter 30 installed at the disk portion 23 blocks the entrance field of the illumination optical system, cuts 99% of the illumination light, and allows only 1% to be transmitted therethrough so as to illuminate the eye to be operated on.

Figure 5:
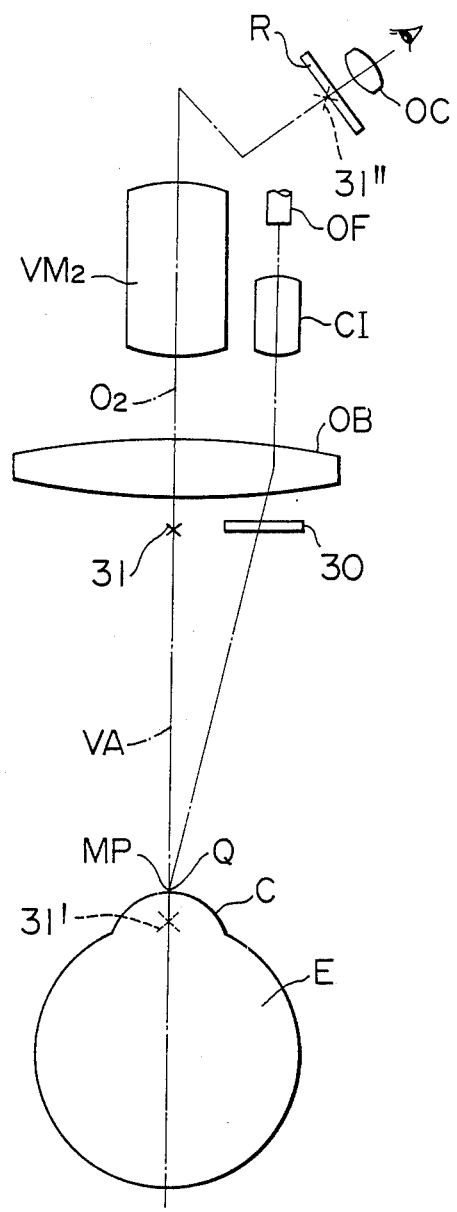
FIG. 5 is a schematic diagram explaining the operation of the gaze-fixing device of the present invention.

Then, as shown in FIG. 5, the eye to be operated on E is made to fixedly gaze at the gaze-fixing target 31. Since the quantity of the illumination light is reduced sufficiently by the ND filter 30, the eye E to be operated on is capable of fixedly gazing at the light of red color from the light emitting diode 31 serving as the gaze-fixing target. Then, the eye to be operated on is capable of fixedly gazing at the gaze-fixing target 31 without any pain by virtue of the synergistic effect derived from both the sufficiently reduced quantity of the light of white color by means of the ND filter and a low degree of the sense of viewing the light of red color from the light-emitting diode 31.

Since the gaze-fixing target 31 is adapted to be located on the optical axis $O_2$ of the zoom optical image formation system VM2 by using this gaze-fixing target as a reference, the visual axis VA of the eye E to be operated on completely coincides with this optical axis $O_2$. The reflected image 31' of the gaze-fixing target 31 formed by the cornea C of the eye to be operated on is formed as an image 31'' of the gaze-fixing target on a reticle R via the single object lens OB, the zoom variable magnification image formation system VM2, and an erect and optical path deflection system. The operator observes this image through the occular OC. At this time, the operator carries out observation through the contacting eye alone on the observation optical system VM2 side and does not use the observation optical system VM1 for the other eye.

Alternatively, an arrangement may be provided such that, by providing a light-shielding plate 50 to the rotary base plate 20, as shown by the alternate long and two short dashes line, as shown in FIG. 2 the light-shielding plate 50 is provided to the rotary base plate 20 for shielding the light for the other eye so as to block the optical path of the zoom variable magnification and image forming system VM1. When this arrangement is adopted, a protrusion 51 is provided on the lens-barrel T for the retraction of the light-shielding plate 50.

Figure 6:
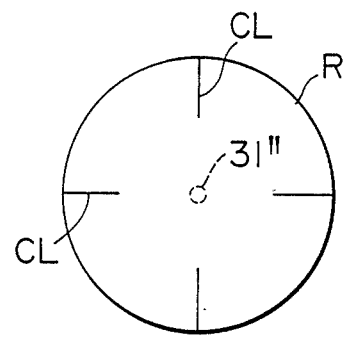
FIG. 6 is a top plan view of a reticle.
Figure 7:
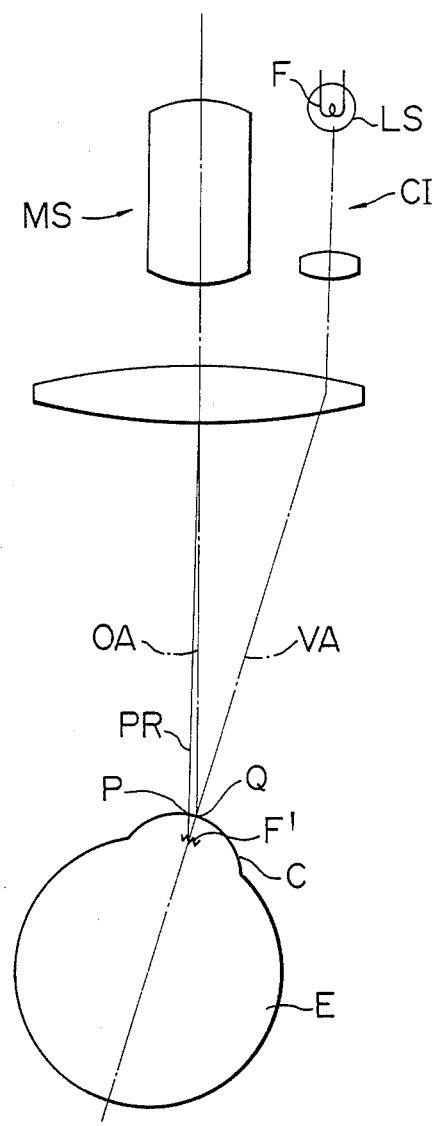
FIG. 7 is a schematic diagram illustrating the arrangement of a conventional example and the operation thereof.

After confirming that the image 31'' of the gaze-fixing target is positioned at the point of intersection of a cross line CL formed on the reticle, as shown in FIG. 6, R, i.e. on the optical axis $O_2$, the operator provides a marking using a known marking device on the cornea at the position which coincides with the image 31'' of the gaze-fixing target. A mark point MP thus marked assures that a marking is provided at the center Q of the cornea by virtue of complete coincidence of the visual axis VA with the optical axis $O_2$.

On completion of the marking, the lever 25 is rotated counterclockwise, and the rotary base plate 20 is moved until the side surface of the arm 24 abuts against the inner wall of the casing 11. This causes the reduction by the ND filter of the quantity of the illumination light to be canceled, and the disk portion 23 and the gaze-fixing target 31 are retracted outside of the optical path for observation without blocking the entrance fields of the zoom variable magnification and image formation systems VM1, VM2. Subsequnetly, using the marking as the reference, the operator performs an RK operation using the two observation optical systems VM1, VM2.

Second Embodiment

Figure 3:
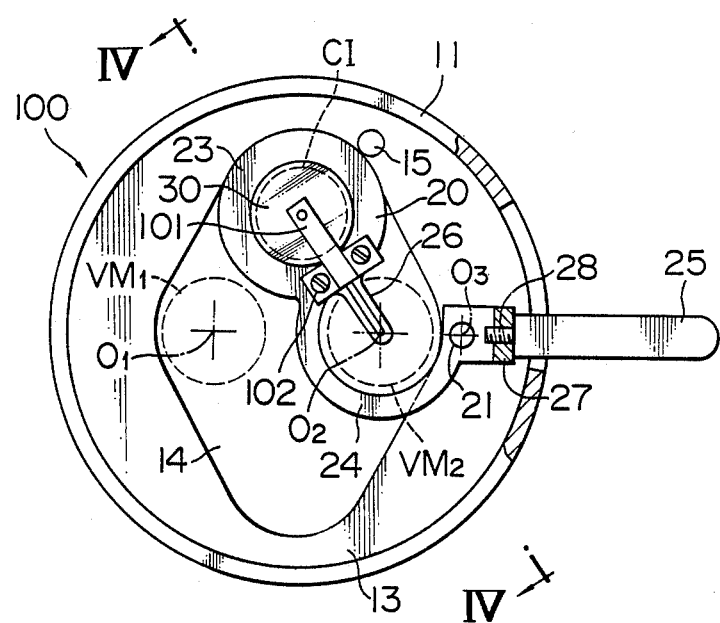
FIG. 3 is a top plan view illustrating a second embodiment of the gaze-fixing device in accordance with the present invention.
Figure 4:
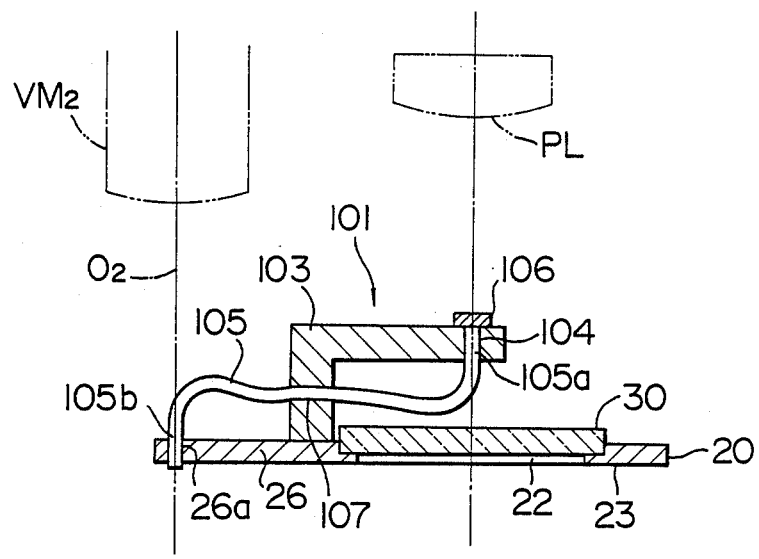
FIG. 4 is a cross-sectional view of FIG. 2 of a gaze-fixing target portion along in accordance with the second embodiment as viewed along the line IV—IV of FIG. 3.

FIGS. 3 and 4 illustrate a second embodiment of the gaze-fixing device in accordance with the present invention. Those component elements that are identical or similar with those of the first embodiment are denoted by the same reference numerals, and redundant description thereof will be avoided. A gaze-fixing device 100 of the second embodiment differs from that of the first embodiment in that although in the first embodiment the light-emitting diode 31 is used as the gaze-fixing target, part of the light from the illumination optical system CI is utilized in the second embodiment.

A gaze-fixing portion 101 is fixed to the disk portion 23 of the rotary base plate 20 in the second embodiment by means of a screw 102. The gaze-fixing portion 101 has a mount 103 having a longitudinal cross-sectional configuration of L-shape, at one end of which is formed a small opening 104 in which is inserted and secured an incident end portion 105a of an optical fiber 105.

In addition, a red color filter 106 is adhered onto the mount 103 so as to be located above the opening 104. The central portion of the optical fiber 105 is inserted in and held by an insertion hole 107 of the mount 105. A light-emitting end portion 105b of the optical fiber 105 is inserted in and secured by an opening 26a formed in the gaze-fixing arm 26 so as to be concentric with the optical axis $O_2$ of the zoom optical image formation system VM2.

By virtue of this arrangement, only the red light component of part of the light from the illumination optical system CI is selectively made to be transmitted by the red color filter, and is made to be incident upon the optical fiber 105. This red color light is to made emerge from the emerge end 105b of the optical fiber 105, and the emerge end surface of this emerge end 105b serves as an gaze-fixing target. On the other hand, 99% of the remaining illumination light form the illumination optical system CI is shielded by the ND filter 30 as in the case of the first embodiment.

As described above, since the gaze-fixing device in accordance with the present invention is arranged such that gaze-fixing target is disposed on the observation optical axis of the microscope, and the light quantity-reducing means for the illumination light for the eye to be operated on, the present invention has advantages in that the device makes it possible to accurately provide a marking used in an RK operation or the like at the central position of the cornea, and that the eye to be operated on is not illuminated with light having more than the required intensity at the time of providing a marking.

The invention has thus been shown with reference to specific embodiments. However, it should be noted that the invention is in no way limited to the details of the illustrated arrangements and may be changed and modified without departing from the scope of the appended claims.

We claim:

1. A gaze-fixing device for a surgical microscope, comprising:
   a gaze-fixing target;
   light quantity reducing means for reducing the quantity of illumination light applied from an illumination light source for illuminating an eye to be operated on; and
   a base plate having said gaze-fixing target and said light quantity reducing means arranged thereon such that they can be simultaneously inserted in and removed from an observation optical axis of the microscope and illumination optical path, respectively, by movement of said base plate.

2. A gaze-fixing device for a surgical microscope according to claim 1, wherein said gaze-fixing target is constituted by a light-emitting end of light-conducting means for receiving part of said illumination light and disposed on said optical axis.

3. A gaze-fixing device for a surgical microscope according to claim 2, wherein said light-conducting means is an optical fiber.

4. A gaze-fixing device for a surgical microscope according to claim 2, wherein said light quantity-reducing means is constituted by an ND filter, and a light-receiving end of said light-conducting means is interposed between said ND filter and said illumination light source.

5. A gaze-fixing device for a surgical microscope according to claim 1, wherein said gaze-fixing target includes a red light emitting diode.

* * * * *